United States Patent [19]

Frederick et al.

[11] Patent Number: 5,145,890
[45] Date of Patent: Sep. 8, 1992

[54] METHOD FOR REDUCING THE CARBOXYLESTER CONTENT OF AN EMULSION POLYMER

[75] Inventors: Clay B. Frederick, Dresher; John R. Udinsky, Ambler, both of Pa.

[73] Assignee: Rohm and Haas Company, Philadelphia, Pa.

[21] Appl. No.: 753,293

[22] Filed: Aug. 30, 1991

[51] Int. Cl.$^5$ ............................................. C08L 89/00
[52] U.S. Cl. ...................... 524/21; 524/832; 435/135; 435/196; 435/262
[58] Field of Search .................. 524/21, 832; 435/135, 435/196, 262

[56] References Cited

U.S. PATENT DOCUMENTS

| | | | |
|---|---|---|---|
| 4,001,081 | 1/1977 | Commeyras et al. | 195/29 |
| 4,090,919 | 5/1978 | Chibata et al. | 524/21 X |
| 4,378,803 | 4/1983 | Takagi et al. | 524/21 X |
| 4,687,807 | 8/1987 | Wetegrove et al. | 524/827 |
| 4,925,797 | 5/1990 | Byrom et al. | 435/135 |
| 4,996,251 | 2/1991 | Farrar et al. | 524/17 |
| 5,077,212 | 12/1991 | Byrom et al. | 435/135 |

FOREIGN PATENT DOCUMENTS

| | | |
|---|---|---|
| 0272026 | 6/1988 | European Pat. Off. . |
| 0393916 | 10/1990 | European Pat. Off. . |
| 2-227465 | 10/1990 | Japan . |

OTHER PUBLICATIONS

M. Dixon et al., "Enzymes", Third Edition, Academic Press, N.Y., 1979, p. 835.

*Primary Examiner*—Joseph L. Schofer
*Assistant Examiner*—J. M. Reddick

[57] ABSTRACT

This invention is directed to a method for reducing the carboxylester content of an emulsion-polymerized addition polymer by contacting the aqueous emulsion polymer with a carboxylesterase enzyme and a reduced carboxylester content emulsion-polymerized addition polymer so prepared.

24 Claims, No Drawings

5,145,890

METHOD FOR REDUCING THE CARBOXYLESTER CONTENT OF AN EMULSION POLYMER

FIELD OF THE INVENTION

This invention relates to a method for reducing the carboxylester content of an emulsion-polymerized addition polymer by contacting the aqueous emulsion polymer with a carboxylesterase, and a reduced organic carboxylester content emulsion-polymerized addition polymer so prepared. More particularly, this invention is directed to a method for reducing the amount of residual ethylenically-unsaturated carboxylester monomer in an emulsion-polymerized addition polymer by contacting the aqueous emulsion polymer with a carboxylesterase.

BACKGROUND OF THE INVENTION

Emulsion-polymerized addition polymers are prepared by the polymerization of ethylenically-unsaturated monomers using ionic- or free radical-initiated and propagated reactions. In most cases these reactions will not proceed to the point of 100% conversion of the ethylenically-unsaturated monomer to polymer within a reasonable time. Elimination of the residual monomer may be desirable due to odor, instability, or toxicity, for example, resulting from the residual monomer. Subsequent elimination of the remaining ethylenically-unsaturated monomer by conversion to polymer by methods such as, for example, heating for prolonged periods, with or without the addition of an ion- or a free radical-source; or physical removal of residual ethylenically-unsaturated monomer by methods such as, for example, vacuum stripping and steam sparging; or conversion to a less undesirable species such as, for example, conversion to a non-volatile adduct have all been disclosed in the past. However, concerns about the toxicity or odor of organic compounds in general, and of ethylenically-unsaturated monomers in particular, have lowered the level of residual ethylenically-unsaturated monomer which is acceptable in emulsion-polymerized addition polymers-levels which are frequently difficult and costly to achieve by conventional techniques. One category of ethylenically-unsaturated monomers is carboxylester monomers wherein at least one carboxylester grouping, —COOR, is present. In addition, ethylenically-unsaturated monomers may contain organic carboxylesters, i.e., compounds bearing at least one ester grouping which are not ethylenically-unsaturated, which persist in the emulsion-polymerized addition polymer. Further, polymerization adjuvants may introduce additional organic carboxylesters, i.e., compounds bearing at least one ester grouping but which may not be ethylenically-unsaturated monomers. Such compounds, too, may give rise to concerns about toxicity or odor. The method of reducing the organic carboxylester content of an emulsion-polymerized addition polymer of this invention by contacting the aqueous emulsion polymer with a carboxylesterase solves these problems.

DESCRIPTION OF THE PRIOR ART

U.S. Pat. No. 4,001,081 discloses a process for the hydrolysis of a nitrile to yield an amide by subjecting the nitrile in aqueous solution to the action of bacteria having a nitrilasic activity, that is a bacteria which has at least one nitrilase capable of catalyzing the hydrolysis of a nitrile to an amide. U.S. Pat. No. 4,001,081 does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

U.S. Pat. No. 4,687,807 discloses a method for reducing the acrylamide present in water-in-oil emulsions of acrylamide polymers with amidase, which amidase may be derived from a broad spectrum of bacterial species. The method comprises adding the amidase to the water-in-oil emulsion of the acrylamide polymer upon completion of its polymerization. U.S. Pat. No. 4,687,807 does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

U.S. Pat. No. 4,925,797 discloses a process for the decomposition of acrylamide using an amidase enzyme in which the enzyme is induced in strains of *Methylophilus methylotrophus*. A method for inducing the enzyme and a process for producing acrylic acid are also disclosed. The process for decomposing acrylamide is disclosed to be useful for reducing the level of unreacted monomer associated with homo- and heteropolymers of acrylamide. U.S. Pat. No. 4,925,797 does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

European Patent Application EP 0 272 026 discloses a process for the decomposition of acrylamide, to a method for the production of the enzyme amidase (acrylamide amidohydrolase EC No. 3-5-1-4) used in the decomposition of acrylamide and to a process for the production of acrylic acid or a salt or ester thereof by decomposition of acrylamide. It is further disclosed that the decomposition process of the invention can be used for decomposing unreacted acrylamide present in polyacrylamide polymers. These acrylamide polymers may be cationic, anionic and nonionic polymers wherein acrylamide may be copolymerized with other monomers, e.g., acrylic acid. EP 0 272 026 does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

European Patent Application EP 0 393 916 discloses a method for producing a microorganism containing elevated levels of an amidase enzyme in which a suitable microorganism is cultivated under certain conditions. Novel microorganisms produced by the method and processes for decomposing acrylamide and for producing acrylic acid are also disclosed. It is further disclosed that the decomposition process of the invention can be used for decomposing unreacted acrylamide present in polyacrylamide polymers. EP 0 393 916 does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

Japanese Patent Application JP02/227,465 A discloses an enzyme-containing resin composition which contains an immobilized enzyme, such as a hydrase or protease, carried physically or chemically on a resin, such as a polystyrene gel, polyacryl gel, acrylic copolymer, polyester condensate, alkyd condensate, polypeptide condensate, or polysaccharide, and a film-forming polymer, such as a lacquer-type vinyl resin, isocyanate crosslinking resin, non-aqueous dispersion resin, aqueous emulsion resin, alkyd resin, alkyd-melamine resin, or polyester-melamine resin. The use of these enzyme-containing resin compositions for a stain-proofing paint and for a paint which prevents the inhabiting and growing of barnacles and seaweed on structures and constructions in the sea. JP02/227,465 A does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

Dixon (M. Dixon, et al., "Enzymes", Third Edition, Academic Press, New York, p.835) discloses hydrolases, a class of enzymes which catalyze the hydrolysis of various bonds. A type of hydrolases are the esterases which include carboxylesterases (Group EC 3.1.1.1 as classified by the Nomenclature Committee of the International Union of Biochemistry), which catalyze the hydrolysis of a carboxylic ester to yield an alcohol and a carboxylic acid anion. Disclosed as sources of carboxylesterase enzyme, also known as carboxylic-ester hydrolase, are animal tissues, plants, molds, and yeast. Dixon does not disclose a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

None of the references teach a method for reducing the organic carboxylester content of an emulsion-polymerized addition polymer by contacting the aqueous emulsion polymer with a carboxylesterase, or a reduced organic carboxylester content emulsion-polymerized addition polymer so prepared.

It is, therefore, an object of this invention to provide a method for reducing the organic carboxylester content in an emulsion-polymerized addition polymer by contacting the aqueous emulsion polymer with a carboxylesterase, and a reduced organic carboxylester content emulsion-polymerized addition polymer so prepared.

It is an additional object of this invention to provide a method for reducing the amount of residual ethylenically-unsaturated carboxylester monomer in an emulsion-polymerized addition polymer by contacting the aqueous emulsion polymer with a carboxylesterase.

It is a further object of this invention to provide a method for reducing the toxicity and/or odor of an emulsion-polymerized addition polymer by contacting the aqueous emulsion polymer with a carboxylesterase.

SUMMARY OF THE INVENTION

A method is provided for reducing the organic carboxylester content of an emulsion-polymerized addition polymer by contacting the aqueous emulsion polymer with a carboxylesterase.

And a reduced organic ester content emulsion-polymerized addition polymer prepared by contacting the aqueous emulsion polymer with a carboxylesterase is provided.

DETAILED DESCRIPTION OF THE INVENTION

This invention is directed to a method for reducing the organic carboxylester content of an emulsion-polymerized addition polymer by contacting the aqueous emulsion polymer with a carboxylesterase, and a reduced organic carboxylester content emulsion-polymerized addition polymer so prepared.

Emulsion-polymerized addition polymers used in the practice of this invention may be prepared by one of many techniques well-known in the art. At least one ethylenically-unsaturated monomer is used to prepare the emulsion-polymerized addition polymer used in the method of this invention. For example, acrylic ester monomers including methyl acrylate, ethyl acrylate, butyl acrylate, 2-ethylhexyl acrylate, decyl acrylate, methyl methacrylate, butyl methacrylate, isodecyl methacrylate, hydroxyethyl acrylate, hydroxyethyl methacrylate, and hydroxypropyl methacrylate; acrylic acid, methacrylic acid, or itaconic acid; amino-functional monomers such as, for example, N,N-dimethyaminoethyl methacrylate; acrylamide or substituted acrylamides such as, for example, N-methylolacrylamide; styrene or substituted styrenes; butadiene; vinyl acetate or other vinyl esters; vinyl ethers; acrylonitrile or methacrylonitrile; and the like, may be used. Low levels of multiethylenically unsaturated monomers such as, for example, allyl methacrylate, diallyl phthalate, 1,4-butylene glycol dimethacrylate, 1,6-hexanedioldiacrylate, and the like, may be used.

Anionic, cationic, or nonionic surfactants, or suitable mixtures thereof, may be used to prepare the emulsion-polymerized addition polymers used in the method of this invention. The polymerization may be carried out by various means such as, for example, with all of the monomer in the reaction kettle at the beginning of the polymerization reaction, with a portion of the monomer in emulsified form present in the reaction kettle at the beginning of the polymerization reaction, and with a small particle size emulsion polymer seed present in the reaction kettle at the beginning of the polymerization reaction. The polymerization reaction may be initiated by various methods known in the art such as, for example, by using the thermal decomposition of an initiator or by using an oxidation-reduction reaction ("redox reaction") to generate free radicals in order to effect the polymerization. Chain transfer agents including mercaptans, polymercaptans, and halogen compounds may be used in the polymerization mixture in order to moderate the molecular weight of the emulsion-polymerized addition polymer. Generally, from 0% to about 1% by weight, based on the weight of the polymeric binder, of $C_4$–$C_{20}$ alkyl mercaptans, mercaptopropionic acid, or esters of mercaptopropionic acid, may be used.

The polymerization reaction may be carried out in a multi-stage process; the particles resulting from such a process may comprise at least two mutually incompatible polymers such as, for example, in core-shell structured particles. Sequential emulsion polymerization processes which are believed to yield core/shell particles are taught in U.S. Pat. Nos. 4,325,856 and 4,654,397, which are hereby incorporated herein by reference. Other modified latex polymer compositions which are believed to contain particles incorporating multiple incompatible polymeric phases are taught in U.S. Pat. No. 4,814,373, which is hereby incorporated herein by reference.

The particle size of the emulsion polymer particles may be in the range of about 40 nanometers to about 5000 nanometers. However, polymodal particle size distributions such as those disclosed in U.S. Pat. Nos. 4,384,056 and 4,539,361, hereby incorporated herein by reference, may be employed.

In most cases the emulsion-polymerized addition polymerization will not proceed to the point of 100% conversion of the ethylenically unsaturated monomer to polymer within a reasonable time. Subsequent conversion of the remaining ethylenically-unsaturated monomer to polymer by methods such as, for example, heating for prolonged periods, with or without the addition of an ion or a free radical source; removal of organic esters by methods such as, for example, vacuum stripping, steam sparging; or conversion to a non-volatile adduct have all been disclosed and may, where suitable, be effected prior to, during, or after effecting the method of this invention.

The emulsion-polymerized addition polymer may contain, in addition, other components such as, for example, emulsifiers, pigments, fillers, anti-migration aids, curing agents, coalescents, wetting agents, biocides, plasticizers, anti-foaming agents, colorants, waxes, or anti-oxidants. If such components are desired to remain in the composition at the levels added, it is preferred that they do not contain organic carboxylester compounds.

This invention is directed to a method for reducing the organic carboxylester content of an emulsion-polymerized addition polymer by contacting the emulsion polymer with a carboxylesterase. By "organic carboxylester" herein is meant an organic molecule wherein at least one ester grouping, —COOR, is present, wherein R is a radical composed of carbon and hydrogen atoms such as, for example, alkyl, branched alkyl, alkenyl, and vinyl. Excluded are R groups bearing polar-hetero atoms such as, for example, 2-hydroxyethyl methacrylate. The organic carboxylester content to be reduced by the method of this invention may include ethylenically-unsaturated organic carboxylester compounds such as, for example, ethyl acrylate, dimethyl itaconate, vinyl acetate, and diallyl phthalate, and may also include organic carboxylester compounds which are not ethylenically-unsaturated such as, for example, ethyl acetate, i-butyl butyrate, dibutyl adipate, and the like. Preferred as organic carboxylesters in the method of this invention are $C_1-C_8$ acrylates, $C_1-C_8$ methacrylates, and vinyl acetate.

In the method of this invention an emulsion-polymerized addition polymer is contacted by a carboxylesterase. Carboxylesterase as used herein is defined as an enzyme of Group EC 3.1.1.1, as classified by the Nomenclature Committee of the International Union of Biochemistry. Known sources of carboxylesterase enzyme, also known as carboxylicester hydrolase, are organisms composed of eukaryotic cells, i.e., cells with nucleii, such as, for example, animal tissues, plants, molds, and yeast. Carboxylesterase which may be used, for example, includes those present in *Aspergillus sp., Rhizoctonia s., Tricoderma h., Cytophagia sp.*, yeast, porcine liver, bovine liver, sheep liver, chicken liver, and the like. Preferred are mammalian carboxylesterase enzymes. Especially preferred is porcine liver carboxylesterase.

Although carboxylesterase enzymes are found in nature such as, for example, in the species disclosed herein-above, recently developed methods may allow the transfer of the carboxylesterase gene to bacteria to facilitate the production of carboxylesterase enzymes, as disclosed in J. Sambrook, et al., "Molecular Cloning: A Laboratory Manual", Second Edition, Cold Spring Harbor Laboratory Press, Plainview, N.Y., 1989, hereby incorporated herein by reference.

The carboxylase must be present in an amount effective to reduce the organic carboxylester content of an emulsion-polymerized addition polymer. The amount of carboxylesterase which is used is preferably from about 0.1 ppm. to about 1000 ppm., by weight based on the weight of the emulsion-polymerized addition polymer. The carboxylesterase is believed to catalyze the hydrolysis of a carboxylic ester to yield an alcohol and a carboxylic acid anion. It is further believed that carboxylic acid compounds are frequently less toxic and/or less volatile in an emulsion-polymerized addition polymer than are their carboxylic ester compound analogs.

The emulsion-polymerized addition polymer may be contacted by the carboxylesterase in any convenient manner such as, for example, by admixing a carboxylesterase with an emulsion-polymerized addition polymer in an emulsion reaction kettle or by passing the emulsion-polymerized addition polymer through a column packed with a carboxylesterase immobilized on a solid support such as, for example, a carboxylesterase immobilized on acrylic beads. The contacting step may take place at pH greater than about 4. Preferred is a pH greater than about 8. The contacting step may take place at a temperature of from about 15° C. to about 95° C. Preferred is a temperature of from about 25° C. to about 65° C.

The following examples are intended to illustrate the method for reducing the organic carboxylester content of an emulsion-polymerized addition polymer by contacting the aqueous emulsion polymer with a carboxylesterase and a reduced organic carboxylester content emulsion-polymerized addition polymer so prepared, to which this invention is directed. They are not intended to limit the invention as other applications of the invention will be obvious to those of ordinary skill in the art.

EXAMPLE 1.

Treatment of an emulsion polymer containing various ethylenically-unsaturated organic carboxylester monomers To 10 g of an aqueous emulsion-polymerized addition polymer [an anionically-stabilized poly(methyl methacrylate/ethyl acrylate/methacrylic acid) composition containing less than 25 ppm. residual ethyl acrylate monomer] at 51% polymer solids, based on the weight of the emulsion, at pH=8.5 contained in a capped, one-ounce, glass vial was added 0.01 g. of ethylenically-unsaturated organic ester monomer, as listed in Table 1.1, to give an emulsion containing 1000 ppm. monomer, based on the weight of monomer+polymer. Then, 1.1 milligrams of protein (110 ppm. enzyme, based on the weight if the emulsion) of a commercial preparation of carboxylesterase enzyme isolated from porcine liver (a suspension in 3.2M. ammonium sulfate solution at pH=8, product number E 3128 from Sigma Chemical Company, St. Louis, MO, with a labelled purity of 230 units of carboxylesterase activity per milligram of protein) was added to give a 110 ppm. solution of the protein (i.e., 0.0011 g. of protein in 10 g. of emulsion). The vial was held at 50° C. for three hours and the reaction was then terminated by removing a 1.0 ml. allquot and mixing it with 9.0 ml. of 0.3% phosphoric acid to give an acidified solution of pH=2.0. The tube was centrifuged at 15,000 rpm. for 20 minutes in a Sorvall RC-5B centrifuge at 0°-5° C. One ml. of the clear supernatant was transferred to a 1.5 ml. HPLC injector vial. An aliquot of 300–500 microliters was injected into a Perkin-Elmer Series 4 pumping system using a Beckman Ultrasphere IP P/N 235335, 5 microns, 4.6 mm.×25 cm. column and a linear gradient solvent system made up of a 0.01M. triethylamine phosphate buffer solution at pH=2 and acetonitrile. Peaks were detected using a combination of a Radiomatic Instruments flowthrough detector and a Hewlett-Packard Diode-array detector. Quantitation was accomplished with a Hewlett-Packard workstation. This instrumention and methodology has been disclosed in deBethizy, et al., Fundamental and Applied Toxicology, Volume 8, pages 549–61 (1987). Monomer removal/hydrolysis was determined relative to a control reaction which did not contain any carboxylesterase; the loss of peak area from the HPLC peak for the parent compound was determined by integration. In cases where carboxylic acid content is reported, the formation of the corresponding ethylenically-unsaturated carboxylic acid was determined by integration. In Table 1.1 "% Hydrolyzed" is defined herein to mean the % of the stated ester monomer HPLC peak which had disappeared after treatment. The results for the treatment of various ethylenically-unsaturated organic ester monomers are given in Table 1.1.

TABLE 1.1

| Reduction of organic carboxylester monomer content | |
|---|---|
| Monomer | % Hydrolyzed |
| Ethyl acrylate | >97 |
| Butyl acrylate | >97 |
| Methyl methacrylate | >97 |
| 2-Ethylhexyl acrylate | 95 |
| Butyl methacrylate | >97 |
| Vinyl acetate[1] | >97 |
| 2-Hydroxyethyl methacrylate | >1 |

[1]Held for 17 hours at ambient temperature.

The organic carboxylester monomer content of an emulsion-polymerized addition polymer was reduced by the method of this invention. 2-Hydroxyethyl methacrylate content was not reduced by the method of this invention.

EXAMPLE 2

Treatment of an emulsion polymer containing various ethylenically-unsaturated organic carboxylester monomers The method of Example 1 was followed with the exceptions that 10 ppm of the same porcine liver carboxylesterase was used and that the monomer/enzyme/emulsion polymer was held at 50° C. for 3 hours except as noted in Table 2.1. Monomer content was determined by analysis of the headspace over the emulsion polymer using conventional gas chromatographic analysis. Results are found in Table 2.1

TABLE 2.1

| Reduction of organic carboxylester monomer content | |
|---|---|
| Monomer | % Hydrolyzed |
| Ethyl acrylate | 99+ |
| Butyl acrylate | 99+ |
| Methyl methacrylate | 99+ |
| 2-Ethylhexyl acrylate | 50 |
| 2-Hydroxyethyl methacrylate | <5 |

The organic carboxylester monomer content of an emulsion-polymerized addition polymer was reduced by the method of this invention. 2-Hydroxyethyl methacrylate content was not reduced by the method of this invention.

EXAMPLE 3.

Effect of pH on the reduction of ethylenically-unsaturated carboxylester monomer content.

To 10 g. of an aqueous emulsion-polymerized addition polymer [an anionically-stabilized poly(methyl methacrylate/ethyl acrylate/methacrylic acid) composition] at 51% polymer solids, based on the weight of the emulsion, at pH=8.5 contained in a capped, one-ounce, glass vial was added 0.01 g. of $^{14}$C-ethyl acrylate to give an emulsion containing 1000 ppm. monomer, based on the weight of monomer+polymer. The pH of the preparations was adjusted up or down with either 5N. sodium hydroxide or 3M. phosphoric acid as presented in Table 3.1. After allowing the mixture to equilibrate for ten minutes at 25° C., 100 ppm of porcine liver carboxylesterase was added. The vial was capped and incubated for 3 hours or 20 hours at ambient temperature. One ml. of the emulsion mixture was removed from the vial and transferred to a 50 ml. NALGENE Oak Ridge polycarbonate tube containing 0.3 ml. 10% phosphoric acid and 8.7 ml. HPLC-grade water. The tube was centrifuged at 15,000 rpm. for 20 minutes in a Sorvall RC-5B centrifuge at 0°-5° C.. One ml. of the clear supernatant was transferred to a 1,5 ml. HPLC injector vial. An aliquot of 300–500 microliters was injected into a Perkin-Elmer Series 4 pumping system using a Beckman Ultrasphere IP P/N 235335, 5 microns, 4.6 mm×25 cm. column and a linear gradient solvent system made up of a 0.01M. triethylamine phosphate buffer solution at pH=2 and methanol. Peaks were detected using a combination of a Radiomatic Instruments flow-through detector and a Hewlett-Packard Diode-array detector. Quantitation was accomplished with a Hewlett-Packard workstation. The results are presented in Table 3.1.

TABLE 3.1

| Effect of pH on reduction of ethyl acrylate content | | | |
|---|---|---|---|
| | | % Hydrolyzed | |
| pH | Adjusting Solution | 3 hours | 20 hours |
| 4.0 | 0.25 ml. H$_3$PO$_4$ | 13 | 15 |
| 5.0 | 0.21 ml. H$_3$PO$_4$ | 22 | 27 |
| 6.0 | 0.17 ml. H$_3$PO$_4$ | 78 | 84 |
| 7.0 | 0.1 ml. H$_3$PO$_4$ | 98 | 99+ |
| 8.0 | 0.07 ml. H$_3$PO$_4$ | 99 | 99+ |
| 10.0 | 0.08 ml. NaOH | 99+ | 99+ |
| 11.0 | 0.14 ml. NaOH | 99+ | 99+ |

The carboxylester monomer content was effectively reduced over a wide pH range by using the method of this invention. Longer contacting time and higher pH increased the reduction of ester monomer content.

EXAMPLE 4.

Effect of temperature on the reduction of ethylenically-unsaturated carboxylester monomer content.

The method of Example 3 was used with the samples at pH=8.5 but the preparations were contacted at the indicated temperature for either 15 minutes or 60 minutes. The results are presented in Table 4.1.

TABLE 4.1

| Effect of temperature on reduction of ethyl acrylate content | | |
|---|---|---|
| | % Hydrolyzed | |
| Temperature (°C.) | 15 min. | 60 min. |
| 40 | 97 | 99+ |
| 50 | 99+ | 99+ |
| 60 | 97 | 99+ |
| 70 | 92 | 93 |

The carboxylester monomer content was effectively reduced over a wide temperature range by using the method of this invention. Temperatures from about 25° C. to about 65° C. are preferred.

EXAMPLE 5.

Effect of storage time on activity of carboxylesterase

The method of Example 3 was followed except that the polymer emulsion and 10 ppm of the porcine liver carboxylesterase were held for various periods of time at 25° C. prior to adding 1000 ppm. of ethyl acrylate. The mixture was then held at 50° C. for 3 hours before quenching and proceeding as in Example 1. The results are presented in Table 5.1.

TABLE 5.1

| Effect of enzyme/emulsion polymer storage time on reduction of ethyl acrylate content | |
|---|---|
| Storage Time (days) | % Hydrolyzed |
| 0 | 99+ |
| 1 | 98 |
| 2 | 95 |
| 3 | 95 |
| 4 | 95 |
| 9 | 94 |
| 17 | 90 |

The carboxylester monomer content was effectively reduced over a wide enzyme/emulsion polymer storage time range. Contacting time, using the method of this invention, may be long without loss of enzyme efficacy in the enzyme/emulsion polymer composition.

EXAMPLE 6.

Effect of enzyme source on the reduction of ethylenically-unsaturated carboxylester monomer content.

The method of Example 3 was used with the exception that the pH for all preparations was held at 8.5 and that the ethyl acrylate/emulsion polymer/enzyme mixture was held at 17-24 hours at ambient temperature before quenching. Each of the enzymes was purchased from Sigma Chemical Co., St. Louis, MO. The results are found in Table 6.1.

TABLE 6.1

| Effect of enzyme source on the reduction of ethyl acrylate (EA) | | | |
|---|---|---|---|
| Enzyme | Source | SIGMA # | % EA Hyd. |
| Acetylesterase | Orange peel | A- 4530 | <1 |
| Lipase Type VII-S | Yeast | L- 9767 | <1 |
| Lipase Type I | Wheat germ | L- 3001 | <1 |
| Lipase Type II | Porcine Pancreas | L-3126 | <1 |
| Yeast Enz. Conc. | Yeast | Y-2875 | 11.7 |
| Yeast Enz. Conc. | Yeast | Y-3000 | 22.6 |
| Lysing Enzyme | Aspergillus sp. | Y-3768 | 29.7 |
| Lysing Enzyme | Rhizoctonia s. | L-8757 | 20.0 |
| Lysing Enzyme | Tricoderma h. | L-2265 | 18.2 |
| Lysing Enzyme | Cytophagia sp. | L-9893 | 18.8 |
| Lyticase | Yeast | L-8012 | 19.6 |
| Carboxylesterase | Porcine liver | E-3128 | 99+ |

The carboxylesterases present in a wide variety of enzyme preparations, including Yeast Enz. Conc., Lysing Enzymes, Lyticase, and porcine liver carboxylesterase, are all effective in reducing ethyl acrylate content, when used in the method of this invention. The Lipase and acetylesterase enzymes, which are not carboxylesterases, are not effective in the method of this invention.

EXAMPLE 7.

Effect of crude enzyme source and preparation method on the reduction of ethylenically-unsaturated carboxylester monomer content.

The method of Example 3 was used with the exception that 400 ppm of crude enzyme (purchased from Sigma Chemical Co., St. Louis, MO) was used and the mixture was held at 55° C. for 3 hours before quenching. The results are presented in Table 7.1.

TABLE 7.1

| Effect of crude enzyme source and preparation method on the reduction of ethyl acrylate (EA) | | | |
|---|---|---|---|
| Preparation | Source | SIGMA # | % EA Hyd. |
| Acetone Powder | Porcine liver | L-8251 | 64.4 |
| Acetone Powder | Goat liver | L-2635 | <1 |
| Acetone Powder | Calf liver | L-7876 | 5.2 |
| Acetone Powder | Bovine liver | L-7751 | 4.3 |
| Acetone Powder | Sheep liver | L-0132 | 14.8 |
| Acetone Powder | Chicken liver | L-8001 | 22.6 |
| Yeast Type I | Yeast | YSC-1 | <1 |
| Brewers Bottom | Yeast | YBB | 2.8 |
| Yeast Extract | Yeast | Y-0375 | <1 |
| Yeast Conc. | Yeast | 20 30 | 11.3 |

Most of the crude enzyme preparations expected to contain carboxylesterase enzyme activity contain sufficient activity to effect a reduction in carboxylester monomer concentration using the method of this invention.

EXAMPLE 8.

Effect of whole liver homogenate on the reduction of ethylenically-unsaturated carboxylester monomer content Sectioned pig liver was obtained fresh from a meat processing plant and frozen immediately on receipt. A 178 g. liver section was allowed to thaw and then placed in ice in a one liter glass beaker containing cold 0.9% sodium chloride solution (saline). The liver section was diced using a pair of surgical sissors. The diced liver was rinsed several times with cold saline to remove the blood, drained, and blotted dry. The liver was homogenized in 1068 ml. Sucrose Versene Tris (SVT) buffer. The homogenization was carried out in the cold using a Brinkman Polytron dismembrator. The entire process required about five minutes. The cold homogenate was transferred to a series of 50 ml. plastic centrifuge tubes and each was spun down at 10,000 rpm. using a Sorval RC-5B centrifuge (Rotor SS-34) for 20 minutes at 0°–4° C. The supernatant was collected and pooled to give 730 ml. post-mitochondrial supernatant (PMS). The PMS was transferred to a one liter glass beaker placed on a magnetic stirrer with the electrode of a Corning Model 12 pH meter dipping into the swirling solution. Dropwise, 3.9 ml. 2.5N. acetic acid was added to the PMS, which brought the pH to 5.50. The thick and turbid mixture was transferred to several 50 ml. plastic centrifuge tubes and spun down at 15,000 rpm. in the Sorvall RC-5B for 20 minutes at 0°–4° C. The 680 ml. of supernatant was discarded; the residue was pooled and resuspended in a total volume of 133.7 ml. with 0.1M. pH=8.0 phosphate buffer (APMS). To the 133.7 ml. APMS, 14.7 ml. of 3.5% TRITON X-100 solution was added dropwise and slowly. The mixture was stirred at room temperature for 30 minutes and the pH was lowered by adding 4.55 ml. 2.5N. acetic acid. The solution was stirred for an additional 15 minutes and then transferred to several 50 ml. centrifuge tubes and spun at 15,000 rpm. in the Sorvall RC-5B centrifuge for 20 minutes at 0°–4° C. The red-colored supernatant was collected and the pH was adjusted to 8.0 with 1N. NaOH solution (APMSX). Then 37.7 g. ammonium sulfate was added with stirring to the ice cold 106.9 ml. of APMSX to get 50% of saturation. This mixture was centrifuged at 15,000 rpm in the Sorvall RC-5B centrifuge for 20 minutes at 0°–4° C. and the supernatant was collected. To this, 15.1 g. ammonium sulfate was added with stirring to achieve 70% of saturation. The centrifugation step was repeated and the supernatant was discarded. The pellet (the salt precipitate) was dissolved in 0.1M. phosphate buffer to yield a final volume of 24 ml. The amount of protein in each preparation was determined by a standard biuret protein assay as is disclosed in A. G. Gornall, et al., *Journal of Biological Chemistry*, Volume 177, pages 751–766 (1949), modified for a Molecular Devices microplate reader.

The method of Example 1 was then followed with the exceptions that the concentration, in ppm. (based on weight of protein) for the various porcine liver fractions, was adjusted to give similar hydrolysis results at the various sampling times and the reactions were carried out using incubation temperatures of 25° and 50° C. The results are presented in Table 8.1.

TABLE 8.1

Effect of various fractions of the whole liver homogenate on the reduction of ethyl acrylate (EA)

| Fraction | Temp. (°C.) | Amt. used | % EA Hydrolyzed | | | | |
|---|---|---|---|---|---|---|---|
| | | | 0 hr. | 1 hr. | 3 hr. | 6 hr. | 8 hr. |
| PMS | 25 | 1000 ppm | 0 | 86 | >99 | >99 | >99 |
| AMPS | 25 | 500 ppm | 0 | 85 | 98 | >99 | >99 |
| AMPSX | 25 | 250 ppm | 0 | 88 | >99 | >99 | >99 |
| SP-1 | 25 | 50 ppm | 0 | 63 | 92 | 95 | >99 |
| SP-1 | 50 | 40 ppm | 0 | 74 | 91 | — | — |
| SP-2 | 50 | 30 ppm | 0 | — | 94 | — | — |
| CP[1] | 50 | 10 ppm | 0 | 91 | 99 | >99 | >99 |
| None | 25 | 0 | 0 | — | — | — | <1 |
| None | 50 | 0 | 0 | — | <1 | — | — |

[1]CP = Commercial Preparation which was Sigma # E 3128 purified porcine liver carboxylesterase preparation.

Whole liver homogenate fractions contain sufficient carboxylesterase activity to effect the reduction of carboxylester monomer content.

EXAMPLE 9.

Effect of 2-methoxyethanol on the effectiveness of reducing the ethyl acrylate content of an emulsion polymer with a carboxylesterase The method of Example 2 was used with the exception that various levels of 2-methoxyethanol (weight % based on polymer weight), as presented in Table 9.1, were added to the enzyme/monomer/emulsion polymer mixture. Results are given in Table 9.1.

TABLE 9.1

Effect of 2-methoxyethanol on reducing the ethyl acrylate (EA) content of an emulsion polymer with a carboxylesterase

| % 2-Methoxyethanol (w/w) | % EA loss |
|---|---|
| 0 | 99+ |
| 1 | 99+ |
| 5 | 99+ |
| 10 | 99 |
| 20 | 97 |
| 30 | 82 |
| 40 | 13 |
| 50 | 6 |

At levels between about 10% and 40% 2-methoxyethanol there may be transesterification of the ethyl acrylate taking place. Otherwise, the loss in ethyl acrylate content corresponds with the formation of acrylic acid. The incorporation of 2-methoxyethanol, a coalescent which may be used in coatings formulations, at levels below about 30% does not have an adverse effect on the reduction of carboxylester monomer content.

EXAMPLE 10.

Treatment of an emulsion polymer containing butyl acrylate with a carboxylesterase; concommitant generation of n-butanol The method of Example 2 was used.

TABLE 10.1

Rate of hydrolysis of butyl acrylate with concommitant generation of n-butanol

| Minutes after esterase addition | ppm butyl acrylate | ppm n-butanol |
|---|---|---|
| 0 | 1200 | 180 |
| 10 | 350 | 350 |
| 20 | 280 | 470 |
| 40 | 200 | 610 |
| 240 | 50 | 950 |

The reduction of butyl acrylate content when using the method of this invention is clear; the concommitant increase in the butanol content implies the concurrent generation of acrylic acid which products are the anticipated products of the carboxylesterase-effected hydrolysis of butyl acrylate.

EXAMPLE 11.

Treatment of an emulsion polymer containing butyl propionate with a carboxylesterase; concommitant generation of n-butanol The method of Example 2 was used.

TABLE 11.1

Rate of hydrolysis of butyl propionate with concommitant generation of n-butanol

| Minutes after butanol esterase addition | ppm butyl propionate | ppm n- |
|---|---|---|
| 0 | 1100 | 270 |
| 10 | 100 | 920 |
| 30 | 30 | 980 |
| 40 | 30 | 1030 |
| 60 | 10 | 900 |

The reduction of butyl propionate content, an organic carboxylester which is not ethylenically unsaturated, when using the method of this invention is clear; the concommitant increase in the butanol content implies the concurrent generation of propionic acid which products are the anticipated products of the carboxylesterase-effected hydrolysis of butyl propionate.

EXAMPLE 12.

Effect of immobilized carboxylesterase on the reduction of ethylenically-unsaturated carboxylesterase monomer content Carboxylesterase enzymes may be immobilized on solid supports to facilitate their use. Carboxylesterase enzymes may be bound to polymeric supports such as, for example, acrylic beads, by various means such as, for example, covalent bonding, without compromising their efficacy. The method of Example 1 was used with a porcine carboxylesterase immobilized on acrylic beads. The immobilized carboxylesterase used was a commercially available material designated E-7259 purchased from Sigma Chemical Company, St. Louis, MO. As supplied 100 mg. of beads at 1 unit of enzyme activity was used to treat 10 g. of emulsion polymer, initially containing 1000 ppm. ethyl acrylate, at room temperature. The results are presented in Table 12.1.

TABLE 12.1

Effect of immobilized carboxylesterase on monomer content

| Contact Time (hours) | % ethyl acrylate loss |
|---|---|
| 3 | 96 |
| 6 | 99 |
| 20 | >99 |

Immobilized carboxylesterase may be effectively used in the method of this invention.

EXAMPLE 13.

Effect of carboxylesterase level on the reduction of ethylenically-unsaturated monomer content The method of Example 1 was used with a purified porcine carboxylesterase at five concentrations. The material used was a commercial preparation designated E-3128 which was purchased from Sigma Chemical Co., St. Louis, MO. The enzyme preparation was used as supplied at 230 units of activity per mg. of protein and as a 1:10, 1:100, 1:1000, and 1:10,000 dilution. A 100 mg. sample of each concentration was used to treat 10 g. of emulsion-polymerized addition polymer initially containing 1000 ppm. ethyl acrylate at room temperature for a contact time of 20 hours in each instance. The results are presented in Table 13.1.

TABLE 13.1

Effect of enzyme concentration on ethyl acrylate content

| Carboxylesterase Concentration (ppm) | % Ethyl acrylate remaining |
|---|---|
| 100 | 1 |
| 10 | 1 |
| 1 | 12 |
| 0.1 | 67 |
| 0.01 | 85 |
| 0 | 90 |

Carboxylesterase concentrations above about 0.01 ppm. are effective in the method of this invention. Preferred are carboxylesterase concentrations above about 1 ppm.

What is claimed is:

1. A method for reducing the organic carboxylester content of an aqueous emulsion-polymerized addition polymer comprising contacting said emulsion-polymerized addition polymer with an amount of a carboxylesterase effective to reduce said organic carboxylester content.

2. The method of claim 1 wherein said emulsion-polymerized addition polymer is adjusted to a pH greater than about 4 prior to said contacting step.

3. The method of claim 1 wherein said emulsion-polymerized addition polymer is adjusted to a pH greater than about 8 prior to said contacting step.

4. The method of claim 1 wherein said contacting step takes place at a temperature of from about 15° C. to about 95° C.

5. The method of claim 1 wherein said contacting step takes place at a temperature of from about 25° C. to about 65° C.

6. The method of claim 1 wherein said carboxylesterase is derived from eukaryotic cells.

7. The method of claim 6 wherein said carboxylesterase is derived from a mammalian source.

8. The method of claim 7 wherein said mammalian source is a porcine liver.

9. The method of claim 1 wherein said carboxylesterase is produced by bacteria, said bacteria comprising a carboxylesterase gene.

10. The method of claim 1 wherein said organic carboxylester is an ethylenically-unsaturated organic carboxylester.

11. The method of claim 10 wherein said ethylenically-unsaturated organic carboxylester is selected from the group consisting of $C_1$–$C_8$ acrylates, $C_1$–$C_8$ methacrylates, and vinyl acetate.

12. The method of claim 1 wherein the amount of said carboxylesterase is from about 0.1 to about 1000 ppm, by weight based on the weight of said emulsion-polymerized addition polymer.

13. An aqueous emulsion-polymerized addition polymer with reduced organic carboxylester content prepared by the process comprising contacting said emulsion-polymerized addition polymer with an amount of a carboxylesterase effective to reduce said organic carboxylester content.

14. The polymer of claim 13 wherein said emulsion-polymerized addition polymer is adjusted to a pH greater than about 4 prior to said contacting step.

15. The polymer of claim 13 wherein the emulsion-polymerized addition polymer is adjusted to a pH greater than about 8 prior to said contacting step.

16. The polymer of claim 13 wherein said contacting step takes place at a temperature of from about 15° C. to about 95° C.

17. The polymer of claim 13 wherein said contacting step takes place at a temperature of from about 25° C. to about 65° C.

18. The polymer of claim 13 wherein said carboxylesterase is derived from eukaryotic cells.

19. The polymer of claim 13 wherein said carboxylesterase is derived from a mammalian source.

20. The polymer of claim 19 wherein said mammalian source is a porcine liver.

21. The polymer of claim 13 wherein said carboxylesterase is produced by bacteria, said bacteria comprising a carboxylesterase gene.

22. The polymer of claim 13 wherein said organic carboxylester is an ethylenically-unsaturated organic carboxylester monomer.

23. The polymer of claim 22 wherein said ethylenically-unsaturated organic carboxylester is selected from the group consisting of $C_1$-$C_8$ acrylates, $C_1$-$C_8$ methacrylates, and vinyl acetate.

24. The polymer of claim 13 wherein the amount of said carboxylesterase is from about 0.1 to about 1000 ppm, by weight based on the weight of said emulsion-polymerized addition polymer.

* * * * *